United States Patent
Ishimoto

(10) Patent No.: US 6,723,987 B2
(45) Date of Patent: Apr. 20, 2004

(54) METHOD OF INSPECTING HOLES USING CHARGED-PARTICLE BEAM

(75) Inventor: Toru Ishimoto, Saitama (JP)

(73) Assignee: Jeol Ltd., Tokyo (JP)

( * ) Notice: Subject to any disclaimer, the term of this patent is extended or adjusted under 35 U.S.C. 154(b) by 245 days.

(21) Appl. No.: 09/727,358

(22) Filed: Nov. 30, 2000

(65) Prior Publication Data

US 2001/0022345 A1 Sep. 20, 2001

(30) Foreign Application Priority Data

Nov. 30, 1999 (JP) .......................................... 11-340569

(51) Int. Cl.[7] ................................................ H05H 3/02
(52) U.S. Cl. ........................ 250/306; 250/307; 250/309
(58) Field of Search ................................. 250/306, 307, 250/309

(56) References Cited

U.S. PATENT DOCUMENTS

| | | | | |
|---|---|---|---|---|
| 5,953,579 A | * | 9/1999 | Lee et al. .................... 250/307 |
| 6,037,588 A | * | 3/2000 | Liu et al. ..................... 250/307 |
| 6,232,787 B1 | * | 5/2001 | Lo et al. ...................... 324/751 |
| 6,323,484 B1 | * | 11/2001 | Ide et al. ..................... 250/306 |
| 6,344,750 B1 | * | 2/2002 | Lo et al. ...................... 250/310 |
| 6,366,688 B1 | * | 4/2002 | Jun et al. ..................... 250/306 |
| 6,426,501 B1 | * | 7/2002 | Nakagawa ............... 250/252.1 |
| 6,559,662 B1 | * | 5/2003 | Yamada et al. ............. 324/751 |

* cited by examiner

Primary Examiner—John R. Lee
Assistant Examiner—Anthony Quash
(74) Attorney, Agent, or Firm—Webb Ziesenheim Logsdon Orkin & Hanson, P.C.

(57) ABSTRACT

A method of inspecting contact holes or via holes in a semiconductor device. Plural small measurement regions Q are established on the whole sample surface. The measurement regions Q are successively irradiated with an electron beam. At this time, an absorption current flowing across the sample is detected and amplified by a current amplifier. A control unit stores data about the absorption current signal derived from the small regions Q in locations of a memory which are addressed corresponding to the positions of the small regions. The control unit reads data about absorption current intensity values from the memory and classifies the intensity values into four intensity ranges, for example, to which different brightness intensities are assigned.

8 Claims, 4 Drawing Sheets

METHOD OF INSPECTING HOLES USING CHARGED-PARTICLE BEAM

BACKGROUND OF THE INVENTION

1. Field of the Invention

The present invention relates to a method of inspecting holes such as contact holes or via holes formed during fabrication processes of semiconductor devices such as ICs and LSIs by the use of a charged-particle beam to examine how the holes are formed.

2. Description of the Related Art

A semiconductor device is fabricated by forming plural layers on a silicon wafer (silicon substrate) for example. In this multilayer structure, an insulator layer is formed between certain layers. Contact holes or via holes are formed in this insulator layer. Conductive interconnects made of a conducting material are buried in the contact holes or via holes, whereby the layers are electrically connected.

Contact holes, for example, are formed by applying a resist on the insulator film, exposing the resist by light according to a contact hole pattern, and then performing a developing step and an etching step during fabrication of the semiconductor device.

During the formation of such contact holes, if the formed contact holes do not exactly pass through the insulator layer, if some of the resist is left behind as a film in the contact holes, or if some of the insulator film is not etched but left behind as a film, then the finally manufactured semiconductor device will malfunction and be regarded as defective.

Therefore, after contact holes are formed, to know how the contact holes are formed is important in determining whether the subsequent process sequence should be carried out. Furthermore, the development step or etching step that is the previous process step is judged to be good or bad, according to the results of the inspection of the state of the formed contact holes. Also, a defect analysis of the process for forming the contact holes can be performed according to the results of the inspection of the state of the formed contact holes.

Inspection of the state of such contact holes can be carried out non destructively by electron beam irradiation from a scanning electron microscope (SEM), for example. Specifically, the electron beam is scanned across the contact holes. A secondary electron image of the contact holes is displayed on the viewing screen of a display device according to secondary electrons detected by the scanning. A person observes the image of the contact holes. In this way, it is possible to know how the contact holes are formed. This technique is described, for example, in U.S. Pat. No. 5,953, 579.

In recent years, elements constituting semiconductor devices have shrunk and have been formed in multiple layers. With this trend, the diameters of contact holes have decreased, and their depths have increased. As a result, the aspect ratio (depth/diameter) of each contact hole has increased. Consequently, the efficiency at which secondary electrons emanating from the hole may be captured has decreased greatly. For this reason, it has become more difficult to grasp the state of the inside or bottom surface of the hole correctly. In addition, it is impossible to know whether the obtained secondary electrons emanate from the opening in the contact hole, from the inner wall surface, or from the bottom. This hinders the inspection for examining how contact holes are formed.

A very large number of contact holes are present over the whole surface of one silicon wafer. If contact holes were inspected one by one, an exorbitantly long time would be necessary. Therefore, the whole wafer surface is partitioned virtually into inspection areas. One contact hole in each inspection area is inspected as a representative one. With this inspection, however, it is not certain whether results of the inspection of the contact hole represent the state of the many etched or developed contact holes existing near the inspected contact hole. Furthermore, where only the results of inspections of a relatively small number of contact holes as described above are used, it is difficult to appropriately judge whether the development step or etching step, that is, a previous process step, is good or not.

SUMMARY OF THE INVENTION

It is an object of the present invention to provide a novel method of inspecting contact holes using a charged-particle beam to permit one to examine how the contact holes are formed.

A method of inspecting holes using a charged-particle beam in accordance with the teachings of the present invention starts with irradiating a sample substrate provided with numerous holes with a charged-particle beam. The state of the holes is inspected, based on a signal obtained by the irradiation of the beam. The charged-particle beam is directed to each inspection region containing holes on the sample substrate. An electrical current flowing between the sample substrate and ground at this time is detected. This sequence of steps is repeated for previously established inspection regions on the sample substrate. In this way, data about the current distribution on the sample substrate is obtained. A map based on brightness is displayed on a display device according to the obtained data about the current distribution.

Other objects and features of the invention will appear in the course of the description thereof, which follows.

DESCRIPTION OF THE PREFERRED EMBODIMENTS

Figure 1:
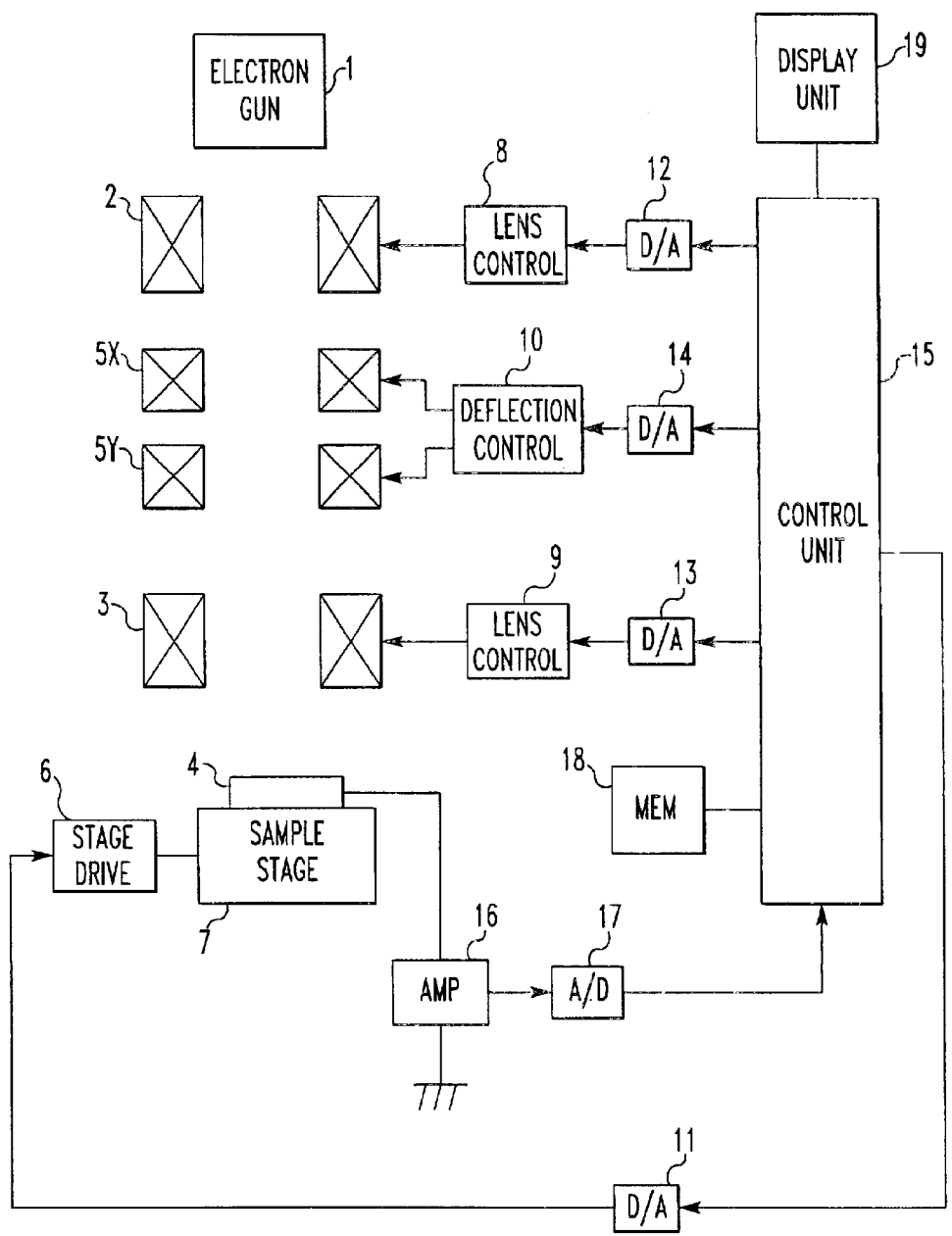
FIG. 1 is a block diagram of an inspection apparatus for implementing a method of inspecting semiconductor devices in accordance with the present invention.

Before describing the preferred embodiments of the present invention, the principle of the present invention is described. In a method of inspecting semiconductor devices in accordance with the present invention, a decision is made as to whether contact holes pass through an insulator film and reach a semiconductor substrate, such as a silicon wafer. Also, a decision is made as to whether the contact holes reach the substrate with a uniform diameter. These decisions are made based on results of a measurement of an absorption current flowing to the substrate through the bottoms of the contact holes. However, the absorption current is a measured electrical current flowing to ground from a conductor line connected with the substrate and so the absorption current produces only a weak signal compared with other signals, such as secondary electrons that are amplified by a detector. Also, the absorption current tends to pick up noise and shows poor response.

On the other hand, contact holes are not processed one by one. Rather, all of the many contact holes over the whole semiconductor substrate are treated by batch processing. Accordingly, the state of penetration of each contact hole depends, for example, on the intensity distribution of a plasma produced in a plasma etcher to open the contact holes and on variations in the state of the chemical reaction of a resist developing solution within the substrate. Consequently, it is quite meaningful to judge how a batch of contact holes over the whole substrate is formed rather than each individual contact hole.

Accordingly, in the present invention, the surface of a semiconductor device in which a large number of contact holes are formed is partitioned into small regions each containing plural contact holes. These small regions are successively irradiated with a charged-particle beam. On each shot of the beam, the absorption current flowing between the substrate and ground is measured. In this way, the absorption current signal distribution over the whole substrate surface is obtained. In consequence, it is possible to know how a batch of contact holes over the whole substrate surface is formed. Preferably, the size and positions of the small regions are so selected that plural contact holes are present within each small region. Where each small region having plural or numerous contact holes in this way is irradiated with the charged-particle beam and the resulting absorption current is measured, the resulting signal is greater than where there is only one contact hole. Hence, noise and response speed problems are mitigated. If only one contact hole is contained within a small region, and if this contact hole is formed distinctively differently from many adjacent contact holes, it is not desirable to represent the state of the adjacent numerous contact holes by the results of measurement of the single contact hole. In contrast, in the method in accordance with the present invention, the electron beam is scanned across plural contact holes in each small region. The results represent average holes. If a special hole is contained in them, its effects can be mitigated greatly. Preferably, the results of measurement represent the state of the surrounding contact holes formed in the region.

FIG. 1 schematically shows an inspection apparatus for carrying out a method of inspecting semiconductor devices in accordance with the present invention. The apparatus has an electron gun 1 that produces an electron beam which is appropriately focused onto a sample 4 such as a wafer by a system of condenser lenses 2 and an objective lens 3. An X-direction deflection coil 5X and a Y-direction deflection coil 5Y scan the electron beam across the sample. This sample 4 is placed on a sample stage 7 that is controllable moved by a stage drive mechanism 6. Lens control circuits 8 and 9 control the excitation strengths of the system of condenser lenses 2 and the objective lens 3, respectively. A deflection control circuit 10 supplies deflection signals to the deflection coils 5X and 5Y. A control unit 15, which issues various instructions and performs various kinds of data processing, sends a Stage-Move instruction, a Lens Control instruction, and a Deflection Control instruction to the stage drive mechanism 6, the lens control circuits 8, 9, and the deflection control circuit 10, respectively, via D/A converters 11, 12, 13, 14, respectively.

A current amplifier 16 detects and amplifies the current (absorption current) flowing through the sample 4. The output from the current amplifier is sent to the control unit 15 via an A/D converter 17. Also shown are a memory 18 and a display unit 19, such as a cathode-ray tube.

Figure 2:
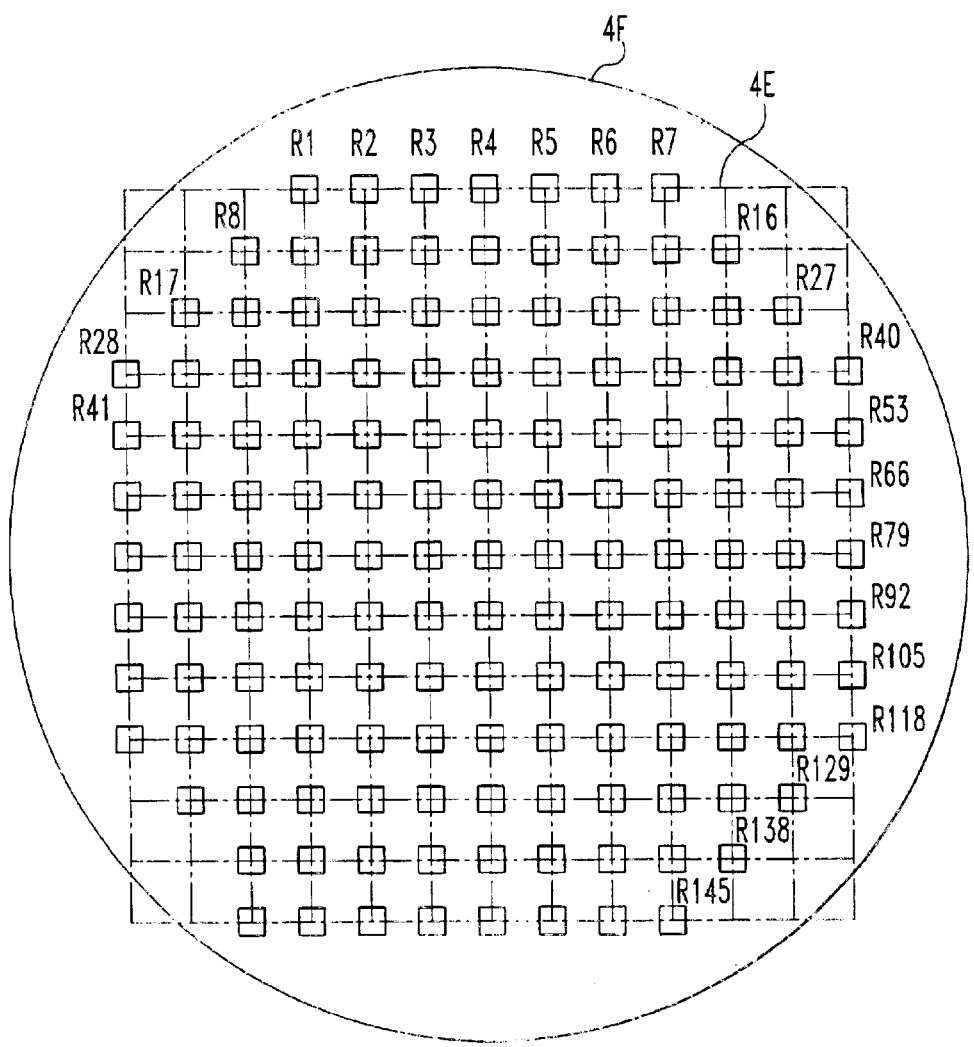
FIG. 2 is a plan view of absorption current measurement regions on an effective area on a sample surface, such as a wafer.
Figure 3:
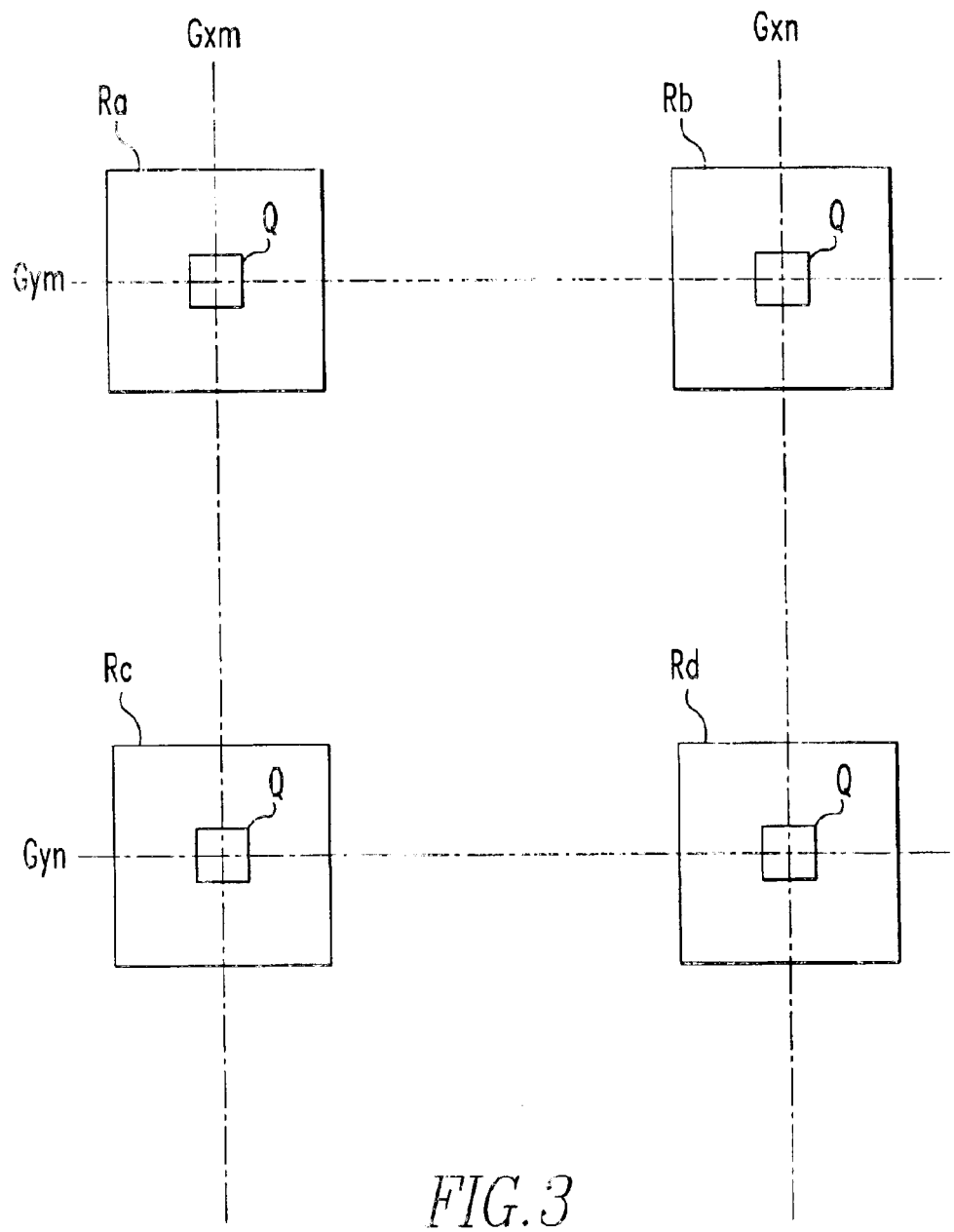
FIG. 3 is an enlarged view of a part of FIG. 2.

A surface of the sample has an effective area 4E (FIG. 2.) on which a semiconductor chip is formed. First, absorption current measurement regions are established over the whole effective area 4E. For example, thirteen vertical and thirteen horizontal virtual grid lines that vertically intersect each other are drawn on the effective area 4E at uniform spacing as shown in FIG. 2. Measurement regions are established around the intersections of the grid lines. Preferably, every measurement region has the same number of contact holes arranged identically. Therefore, the spacing between the grid lines and their positions are so set that identical parts (e.g., rectangular regions in the centers of chip patterns) of repeatedly formed chip patterns on the sample are located at grid points. In FIG. 2, chip patterns on which measurement regions are established are indicated by R1, R2, R3, R4, R5, . . . , R145. Each region actually irradiated with the electron beam is a small region Q measuring 0.1 mm×0.1 mm to 1 mm×1 mm, as shown in FIG. 3, taking account of a scan width of about 1 mm in which deflection distortion of the electron beam is tolerated. A certain number of contact holes are formed within this small region. In FIG. 3, indicated by Gxm, Gxn, Gym, and Gyn are grid lines. Chip pattern regions Ra, Rb, Rc, and Rd correspond to R1, R2, R3, R4, R5, . . . , R145 described above. Each small region Q is irradiated with the electron beam in the manner described below.

Exciting signals from the lens control circuits 8 and 9 control the excitation of the system of condenser lenses 2 and the objective lens 3, respectively. In this way, the degree of focusing of the electron beam is adjusted such that the beam is sharply focused onto the sample. The sample stage is moved in steps such that the center of each small region Q within the regions R1, R2, R3, R4, R5, . . . , R145 is brought to the center of the optical axis of the electron beam (the scanning center of the electron beam) in turn, when each small region Q is at rest in the center position of the electron beam, the whole surface of each small region Q is scanned once or more with the sharply focused electron beam. In this example, the electron beam is focused sharply and scanned across each small region Q. Alternatively, the cross-section size of the electron beam may be made to correspond to the size of each small region Q on the sample, and each small region may be irradiated with the beam for a given time in a static manner.

When each small region Q is being scanned with the electron beam, the absorption current flowing through the sample 4 is amplified by the current amplifier 16 and integrated over the scanning period. The absorption current detected and integrated in this way contains information indicating on the average how the plural contact holes have been formed within the small region Q.

If resist is left behind within the contact hole or unetched insulator film remains, and if the left behind resist or film is irradiated with the electron beam, charge effects will be produced. However, the charge effects are not large enough that detection of the absorption current is made impossible. However, for other cause (i.e., charge effects produced when the electron beam hits other than contact holes), measurement of the absorption current may be made infeasible. Accordingly, when the sample 4 is irradiated with the electron beam, secondary electrons emanating from the sample 4 can be detected by a normally mounted secondary electron detector (not shown). A secondary electron image may be displayed on a display unit (which may be the display unit 19 or a separate display unit) according to the output from the secondary electron detector. The extent of the charging effects is judged from the displayed image. Finally, the probe current is determined from the results. As a result, the charging effect on the sample is minimized. Also, noise introduced to a distribution image or other image displayed on the display unit 19 as described later is reduced.

An absorption current signal derived from each small region Q within the chip patterns R1, R2, R3, R4, R5, . . . , R145 is fed to the control unit 15 via the A/D converter 17 in turn. The control unit 15 stores 145 data items about the absorption current signal derived from the small regions Q in locations of the memory 18 which are addressed corresponding to the coordinates (positions) of the small regions.

Figure 4:
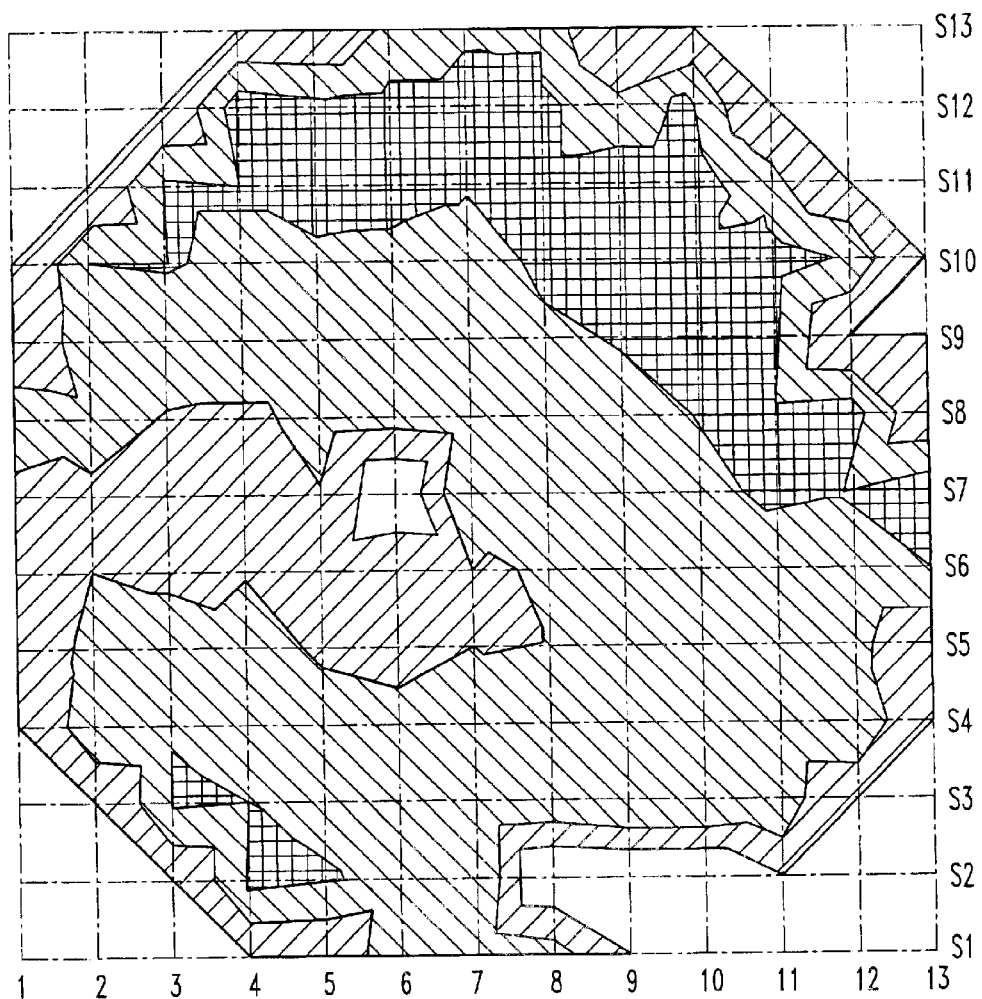
FIG. 4 is a contour map-like graphical representation of the absorption current distribution over the whole sample provided on the viewing screen of a display device 19 shown in FIG. 1.

Then, the control unit 15 reads the 145 data items about the intensities of the absorption current from the memory 18, the data items having been obtained from the whole surface of the sample. The control unit 15 displays a map of absorption current intensities on the viewing screen of the display unit 19 according to the data items read out. As an example of the map display, absorption current intensities are classified into four intensity ranges. Four brightness values or four different colors are assigned to the four intensity ranges, respectively. A grid consisting of 13×13 grid lines, for example, is displayed on the viewing screen. A dot having a size determined taking account of the grid line spacing is displayed in each grid point. The brightness value or color of this dot is set according to the intensity range to which the absorption current intensity arising from this grid point belongs. In consequence, the distribution of the absorption current intensities derived from the whole wafer surface is displayed by 145 dots. This would inevitably provide a rough image quality, since only 145 dots are used to represent the grid points. If displayed points are added among the 145 dots by an interpolation technique or other technique, then a finer map can be displayed. FIG. 4 shows an example of such a display. Data about many points among the grid points are found by an interpolation technique using the above-described data. The results are displayed as shown in FIG. 4, where the distribution of the absorption current intensities obtained from the whole wafer sample are displayed on the viewing screen of the display unit 19 in terms of four brightness values or four different colors. This display method is known as contour representation.

In this way, in the present invention, the whole effective surface of a sample, such as a wafer, is partitioned into plural small regions each containing plural contact holes, and the small regions are successively illuminated with an electron beam to measure absorption current values. Thus, the distribution of absorption current values derived from the whole sample is obtained. Consequently, it is assured that one can judge how the contact holes over the whole sample or contact holes in a part of the sample are etched or developed.

By displaying the distribution of absorption current values arising from the whole sample in terms of a contour map, the differences in tendency among various portions of a sample to be processed become apparent. Hence, a decision as to whether a development step or an etching step that is a previous process step has been performed well can be made appropriately. Furthermore, this contour representation is helpful in judging which contact hole portions should be subjected to defect analysis.

In the embodiment described above, one small region around an intersection of grid lines within a chip pattern is illuminated with an electron beam, and the absorption current is measured. Alternatively, plural small regions may be illuminated with the electron beam, and the absorption current may be measured.

Where each small region Q is scanned plural times, an integral value is obtained from these plural scans. An average value may be obtained from the integral value. This average value may be used as a measurement value derived from the small region.

Furthermore, in the above embodiment, when locations at which absorption current is measured are established on the effective area on a sample surface, thirteen vertical and thirteen horizontal grid lines that intersect each other perpendicularly are virtually drawn on the sample surface. The number of the grid lines is not limited to this example. If the number of the grid lines is increased and the number of the measurement regions is increased, then the accuracy of the distribution of absorption current values over the whole sample is enhanced. However, the number of measurements is increased accordingly. If the number is reduced below the above value, the accuracy of the distribution is deteriorated. However, the number of measurements is reduced accordingly.

In addition, in the above embodiment, the absorption current values derived from measurement points are classified into different ranges to which different brightness values or different colors are assigned. Thus, the distribution of the absorption current values arising from the whole sample is displayed. Alternatively, the standard deviation at each measurement point may be found based on data derived from all the measurement points. The standard deviation values may be classified into different ranges to which different brightness values or different colors are assigned. In this way, the distribution of absorption current values based on standard deviations may be displayed.

The control unit 15 has been previously set at threshold values for the classification. The control unit 15 may also be set at other threshold values. The control unit regards absorption current values which are obtained by measurements or calculations and less than the latter threshold value as abnormal absorption values. Those portions (hereinafter referred to as abnormal portions) of the brightness distribution displayed on the viewing screen of the display unit 19 which are attributed to these abnormal absorption values may be displayed in a form distinguishable from the other portions. For example, these abnormal portions may be displayed in different colors or blinked on and off. In the case of color map representation, the abnormal portions may be displayed in a color different from other colors or may be blanked. At this time, the standard deviation of absorption current values measured from each small region may be found, and those standard deviations which are in excess of a threshold value different from the threshold values used for classification may be regarded as abnormal.

Further, in the above embodiment, the sample is irradiated with an electron beam. Instead, an ion beam may be used.

Having thus described my invention with the detail and particularity required by the Patent Laws, what is desired protected by Letters Patent is set forth in the following claims.

What is claimed is:

1. A method of inspecting the state of completeness of the formation of a large number of holes formed in a wafer sample by directing a charged-particle beam to the sample and obtaining resulting signals, said method comprising the steps of:

establishing measurement regions containing holes on the sample;

directing said charged-particle beam for a given time period to the measurement regions on the sample containing the holes;

detecting an electrical current flowing through the wafer sample to ground for each of said measurement regions;

finding data about accumulative or averaged current distribution on the sample from detected values of electrical current; and displaying a brightness-based map on a display unit according to said found data about the current distribution during the given time period.

2. The method of claim 1, wherein size and positions of said measurement regions are so set that plural holes are present within each of said measurement regions.

3. The method of claim 1, wherein the regions irradiated with said charged-particle beam are located in identical positions within periodic patterns formed on said sample.

4. The method of claim 1, wherein said charged-particle beam is scanned across each of said measurement regions, and wherein said electrical current is accumulated during scan and a resulting value is used as a measurement value derived from each measurement region.

5. The method of claim 1, wherein said charged-particle beam is scanned across each of said measurement regions, and wherein an average value of said electrical current during the scanning period is used as a measurement value derived from each measurement region.

6. The method of claim 1, wherein each of said measurement regions is totally irradiated with said charged-particle beam for a given time in a static manner, and wherein said electrical current is accumulated during the given time and a resulting value is used as a measurement value derived from each measurement region.

7. The method of claim 1, wherein each of said measurement regions is totally irradiated with said charged-particle beam for a given time in a static manner, and wherein an average value of said electrical current is used as a measurement value derived from each measurement region.

8. A nondestructive method of inspecting the state of completeness of the formation of a large number of holes formed in a wafer sample by directing a charged-particle beam to the sample and obtaining resulting signals, said method comprising the steps of:

establishing measurement regions containing holes on the sample such that size and positions of said measurement regions are so set that plural holes are present within each of said measurement regions and the regions are located in identical positions within periodic patterns formed on said sample;

directing said charged-particle beam to the measurement regions on the sample containing the holes;

detecting an electrical current flowing through the wafer sample to ground for each of said measurement regions for a given time period;

finding data about accumulative or averaged current distribution on the sample from detected values of electrical current; and displaying a brightness-based map on a display unit according to said found data about the current distribution during the given time period.

* * * * *